(12) United States Patent
Cleathero (10) Patent No.: US 9,956,344 B2
(45) Date of Patent: May 1, 2018

(54) AUTOINJECTOR

(75) Inventor: Ian Cleathero, Leicestershire (GB)

(73) Assignee: THE MEDICAL HOUSE LIMITED, Hertfordshire (GB)

( * ) Notice: Subject to any disclaimer, the term of this patent is extended or adjusted under 35 U.S.C. 154(b) by 1162 days.

(21) Appl. No.: 13/387,190

(22) PCT Filed: Jul. 30, 2010

(86) PCT No.: PCT/GB2010/051257
§ 371 (c)(1),
(2), (4) Date: May 22, 2012

(87) PCT Pub. No.: WO2011/012903
PCT Pub. Date: Feb. 3, 2011

(65) Prior Publication Data
US 2012/0253289 A1    Oct. 4, 2012

(30) Foreign Application Priority Data

Jul. 31, 2009 (GB) .................................. 0913385.1

(51) Int. Cl.
*A61M 5/20* (2006.01)
*A61M 5/315* (2006.01)
(Continued)

(52) U.S. Cl.
CPC .......... *A61M 5/2033* (2013.01); *A61M 5/002* (2013.01); *A61M 5/31571* (2013.01);
(Continued)

(58) Field of Classification Search
CPC ................ A61M 5/2033; A61M 5/002; A61M 5/31571; A61M 5/3257; A61M 5/31591;
(Continued)

(56) References Cited

U.S. PATENT DOCUMENTS 5,106,379 A    4/1992  Leap
5,222,947 A    6/1993  D'Amico
(Continued)

FOREIGN PATENT DOCUMENTS

FR    2342079    10/1977
GB    2202747    10/1988
(Continued)

OTHER PUBLICATIONS

International Search Report dated Jul. 30, 2010 for PCT/GB2010/051257.
(Continued)

*Primary Examiner* — Bhisma Mehta
*Assistant Examiner* — Jenna Zhang
(74) *Attorney, Agent, or Firm* — Stoel Rives LLP (57) ABSTRACT

An autoinjector including: a housing, in which can be mounted a syringe (28) having a plunger, a barrel and needle (19) at one end thereof through which medicament can be delivered to an injection site,—a syringe support means (30) capable of causing said syringe to move along an axial path with respect to said housing; biasing means capable of biasing said syringe support means so that said needle is normally inside said housing; and engagement means (180) selectively moveable by a user from a first position in which rearward movement of the syringe along said axial path is substantially prevented when said syringe is in an extended position where at least part of said needle is out of the housing, to a second position in which rearward movement of the syringe along said axial path relative to said housing is possible and said biasing means causes said needle to retract inside said housing; wherein said housing includes an outer housing (16) and said autoinjector further comprises a sleeve (18) intermediate the syringe support means and said outer housing that is capable of moving the engagement
(Continued)

means between said first and second positions by rotating said sleeve about a longitudinal axis of said autoinjector between a first rotational position and a second rotational position; and wherein the sleeve is moveable between said first and second rotational positions by moving said outer housing with respect to the sleeve in a substantially axial direction.

23 Claims, 7 Drawing Sheets

(51) Int. Cl.
*A61M 5/32* (2006.01)
*A61M 5/00* (2006.01)

(52) U.S. Cl.
CPC ...... *A61M 5/31591* (2013.01); *A61M 5/3257* (2013.01); *A61M 5/3158* (2013.01); *A61M 5/31555* (2013.01); *A61M 5/3204* (2013.01); *A61M 5/3271* (2013.01); *A61M 2005/206* (2013.01); *A61M 2005/2013* (2013.01); *A61M 2005/2073* (2013.01)

(58) Field of Classification Search
CPC ............ A61M 5/31555; A61M 5/3158; A61M 5/3204; A61M 2005/2073; A61M 2005/2013; A61M 2005/206
See application file for complete search history.

(56) References Cited

U.S. PATENT DOCUMENTS

| | | | | |
|---|---|---|---|---|
| 5,320,609 | A * | 6/1994 | Haber | A61M 5/2033 604/135 |
| 5,472,430 | A | 12/1995 | Vaillancourt et al. | |
| 5,695,475 | A | 12/1997 | Best, Jr. et al. | |
| 5,984,899 | A | 11/1999 | D'Alessio et al. | |
| 6,171,284 | B1 | 1/2001 | Kao et al. | |
| 6,210,369 | B1 * | 4/2001 | Wilmot | A61M 5/2033 604/157 |
| 6,270,479 | B1 * | 8/2001 | Bergens | A61M 5/2033 604/156 |
| 6,527,742 | B1 * | 3/2003 | Malenchek | A61M 5/3272 604/110 |
| 7,118,552 | B2 * | 10/2006 | Shaw | A61M 5/326 604/110 |
| 7,976,499 | B2 * | 7/2011 | Grunhut | A61M 5/2033 604/110 |
| 2003/0105430 | A1 * | 6/2003 | Lavi | A61M 5/2033 604/136 |
| 2004/0039336 | A1 * | 2/2004 | Amark | A61M 5/2033 604/136 |
| 2008/0195056 | A1 * | 8/2008 | Bishop | A61M 5/2033 604/218 |
| 2010/0185178 | A1 * | 7/2010 | Sharp | A61M 5/002 604/506 |

FOREIGN PATENT DOCUMENTS

| | | |
|---|---|---|
| GB | 2396298 | 6/2004 |
| WO | WO 1999/053979 | 10/1999 |
| WO | 2001093926 | 12/2001 |
| WO | WO 2002/089878 | 11/2002 |
| WO | 2003099358 | 12/2003 |
| WO | 2005070481 | 8/2005 |
| WO | WO 2007/026163 | 3/2007 |
| WO | WO 2007/077463 | 7/2007 |
| WO | WO 2008/110332 | 9/2008 |
| WO | WO2008/113864 | 9/2008 |
| WO | WO 2008/113864 | 9/2008 |
| WO | WO2009/063030 | 5/2009 |
| WO | WO 2009/063030 | 5/2009 |
| WO | 2009127861 | 10/2009 |

OTHER PUBLICATIONS

International Preliminary Report and Written Opinion dated Feb. 9, 2012 for PCT/GB2010/051257.

* cited by examiner

AUTOINJECTOR

CROSS-REFERENCE TO RELATED APPLICATIONS

This application is a national stage application under 35 U.S.C. § 371 of International Application No. PCT/GB2010/051257, titled IMPROVED AUTOINJECTOR, filed Jul. 30, 2010, which claims priority to Great Britain Patent Application No. 0913385.1, filed Jul. 31, 2009, both of which are hereby incorporated by reference in their entireties.

This invention relates to the field of autoinjectors for delivering a dose of medicament and, in particular, the invention relates to autoinjectors having a mechanism to control the retraction of the needle from an injection site.

BACKGROUND

An autoinjector is an automatic injection device designed to facilitate automated delivery of a dose of medicament to a patient through a hypodermic needle, the injection usually being administered by the patient themselves. An autoinjector works, for example, by delivering an injection automatically upon actuation by the patient pressing a button, moving a lever or part of a housing etc. This is in contrast to a conventional manual syringe where a plunger must be manually depressed into a barrel containing medicament in order to effect the injection. The terms "autoinjector" and "injection device" are used interchangeably in the following description.

Examples of autoinjectors are described in WO2003/099358 (Seedlings Life Science Ventures LLC) and WO01/93926 (Mayo Foundation for Medical Education and Research). These are both generally flat devices which are of small size to encourage users to carry the device with them for ready access. GB2396298 (PA Consulting Services Ltd) is an example of a more conventionally-shaped elongate autoinjector, but of relatively complex internal construction.

All three of the above prior art devices have a custom designed medicament chamber therein rather than being built around a standard pre-filled syringe presentation. The custom medicament chamber, although allowing for a compact overall size for the device, means that the device as whole must be subjected to more rigorous regulatory control as compared with a device containing a standard pre-filled syringe presentation which will have already obtained regulatory approval.

In general, an autoinjector includes a needle which is located within the housing of the device. Upon activation of a force-generating source, a portion of the needle extends out of the housing and penetrates the outer layer of skin to deliver medicament. In some known autoinjectors, after activation, a needle cover or needle shield moves forward to conceal the needle after use. In GB2396298, the needle automatically retracts back into the housing by means of a biasing spring.

An improved autoinjector is described in our international patent application, published under number WO 2005/070481. This device requires that the needle is moved axially so that it can appear beyond the end of the nozzle for the duration of the injection, after which the needle retracts automatically, so that it is never in sight of the user. The device also requires that the plunger is moved axially so that medicament is ejected. The overall complexity of the autoinjector is significantly reduced by both of these requirements being effected by one component, namely an inner housing, and the device has the significant advantage that it can be built around a conventional or standard syringe presentation.

The injection device of WO 2005/070481 is designed to be used in conjunction with a standard drug presentation e.g. a pre-filled syringe comprising a needle, a barrel pre-filled with medicament and a plunger. The plunger may include a separately-provided plunger rod. As mentioned above, there is a significant commercial advantage in being able to use a standard pre-filled syringe, which will have been subjected to numerous clinical trials, drug stability studies and regulatory approval. Any modification to the standard syringe may require further trials and approval, adding delay and expense.

An improved autoinjector device is described in WO 2009/127861 (The Medical House Limited) wherein the needle does not automatically retract back into the device immediately after a dose of medicament has been delivered. Instead, in the device of WO 2009/127861, the user selectively actuates the retraction of the needle when desired. This may be by removing the device from the injection site, or by actuating some other trigger means. It is known that, in some cases, automatic retraction is undesirable as excessively quick retraction of the needle after delivery may cause the medicament to escape from the puncture hole created by the needle in the tissue. This is especially true if the liquid has not dispersed into the tissue and is in a "pressurised bolus" at the point of delivery which is a known problem when injecting adrenaline, for example. The device of WO 2009/127861 therefore mitigates these problems by allowing the retraction of the needle to be manually controlled or at least delayed.

It is an object of the present invention to provide an alternative and/or improved solution to the above-mentioned known problems associated with automatic retraction autoinjector devices.

BRIEF SUMMARY OF THE DISCLOSURE

In accordance with the present invention there is provided an autoinjector including
- a housing, in which can be mounted a syringe having a plunger, a barrel and needle at one end thereof through which medicament can be delivered to an injection site;
- a syringe support means capable of causing said syringe to move along an axial path with respect to said housing;
- biasing means capable of biasing said syringe support means so that said needle is normally inside said housing,
- engagement means selectively moveable by a user from a first position in which rearward movement of the syringe along said axial path is substantially prevented when said syringe is in an extended position where at least part of said needle is out of the housing, to a second position in which rearward movement of the syringe along said axial path relative to said housing is possible and said biasing means causes said needle to retract inside said housing;
- wherein said housing includes an outer housing and said autoinjector further comprises
- a sleeve intermediate the syringe support means and said outer housing that is capable of moving the engagement means between said first and second positions by rotating said sleeve about a longitudinal axis of said autoinjector between a first rotational position and a second rotational position;

wherein the sleeve is moveable between said first and second rotational positions by moving said outer housing with respect to the sleeve in a substantially axial direction.

Therefore, the present invention facilitates controlled retraction of the needle by movement of the outer housing in an intuitively substantially axial direction. The rotational component, i.e. the sleeve, is within the outer housing, so the user does not feel or see any rotating components. Thus, the autoinjector of the present invention may appear to the user to be substantially identical to the autoinjector of WO 2005/070481, whilst affording the user control over the retraction of the needle.

In a preferable embodiment, said housing further includes an inner housing, at least part of which is positionable, in use, intermediate the outer housing and the syringe support means; and a rear housing intermediate said outer housing and said inner housing, and wherein said autoinjector further comprises an energy source in communication with said inner housing, the inner housing being moveable by the energy source between three positions, namely a first position in which the inner housing is in communication with the barrel such that, in use, the plunger and barrel are movable axially so as to move at least part of said needle out of the outer housing;

a second position in which the inner housing is in communication with the plunger but not the barrel such that, in use, said plunger is movable axially into said barrel so as to expel medicament through the needle; and a third position in which the inner housing is in communication with neither the plunger nor the barrel such that, in use, the plunger and barrel are able to retract in order to retract the needle into the outer housing.

In this preferable embodiment, the needle penetration, medicament delivery and needle retraction are all controlled by a single component (i.e. the inner housing), making the operation of the device particularly reliable and efficient. In addition to the inner housing being out of communication with the plunger and barrel, the blocking means must also be in the second position for needle retraction to take place.

Preferably, said engagement means is selectively moveable by a user from said first position to said second position by the release or reduction of a previously-applied forward force. Further preferably, said engagement means is selectively moveable by a user from said first position to said second position by the release or reduction of the previously-applied forward force after delivery of a partial, but not necessarily complete, dose of medicament. Said engagement means preferably forms part of said sleeve. Therefore, in this preferable embodiment, the needle can be retracted before an entire dose of medicament has been delivered.

In said first position said blocking means preferably engage with the syringe support means to substantially prevent rearward movement of the syringe along said axial path. Preferably, said sleeve comprises biasing means for urging the sleeve towards the second rotational position.

Preferably, said housing further comprises a front housing, said front housing being disposed at least partially within the outer housing at a forward end of the autoinjector; and wherein engagement between said syringe support means and said front housing restricts movement of the syringe support means to axial movement relative to the front housing.

Preferably, said front housing has a plurality of axial slots and the syringe support means includes projections that engage with said axial slots to restrict said relative movement between the syringe support means and the front housing to relative axial movement.

Said sleeve preferably comprises a plurality of legs projecting axially forwardly, wherein said legs each have a foot projecting radially inwardly.

Said syringe support means preferably comprises a plurality of tabs projecting radially outwardly and said tabs are axially aligned with said feet when said sleeve is in said second rotational position.

Preferably, forward axial movement of the syringe support means relative to said sleeve is substantially prevented by abutment between said tabs and said feet when said sleeve is in said second rotational position and said tabs are disposed axially rearwards of said feet.

Said tabs preferably comprise guide ribs that extend in both an axially rearward direction and a circumferential direction from said tabs, where, during assembly of the autoinjector, said guide ribs are capable of abutting said feet and rotating said sleeve away from said second rotational position so that said feet can move from a position axially rearward of said tabs to a position axially forward of said tabs. Preferably said sleeve is capable of rotating back to said second rotational position when said feet are positioned axially forward of said tabs. Said feet are preferably generally wedge-shaped.

Preferably, said engagement means include blocking means which comprise said feet and a plurality of flexible beams are each connected to said syringe support means at a proximal end and extend both radially outwardly and axially rearwardly to a distal end, where said beams are axially aligned with said feet when said sleeve is in said first rotational position, such that in use, as the syringe support means moves axially forward relative to the sleeve, said beams are capable of contacting said feet and deflecting radially inwardly until said distal ends are axially forwards of said feet and when positioned axially forwards of said feet said beams are capable of flexing radially outwards to a position where said distal ends are axially aligned with or radially beyond said feet.

Said inner housing preferably comprises a set of rear tags and a set of forward tags where said rear tags are capable of communicating with the plunger and said forward tags are capable of communicating with the barrel. Said rear tags and said forward tags are preferably radially flexible.

Preferably, said sleeve comprises a plurality of longitudinal ribs on an inner surface, and an outer surface of each rear tag of said inner housing has a radially extending abutment element where said abutment elements are axially aligned with said longitudinal ribs when said sleeve is in said first rotational position. Said abutment elements are preferably tapered in a circumferential direction. Said engagement means preferably include the rear tags, wherein abutment between said longitudinal ribs and said abutment elements preferably causes said rear tags to flex radially inwardly into communication with said plunger when said sleeve is in said first rotational position. Said communication between said rear tags and said plunger is preferably radial gripping of the rear tags on the plunger, or, additionally or alternatively, the communication is axial blocking of the plunger by the rear tags, where the rear tags are axially aligned with and axially rearward of the plunger. In either case, said longitudinal ribs are preferably tapered at a rear end in an axial direction.

Preferably, said rear housing comprises apertures and said front tags are capable of flexing radially outwardly into said apertures into said second position where said inner housing is not in communication with said barrel.

BRIEF DESCRIPTION OF THE DRAWINGS

Preferred embodiments of the present invention will now be more particularly described, by way of example only, with reference to the accompanying drawings in which.

DETAILED DESCRIPTION

Throughout the following description, reference to a "forward" direction means the direction which is towards the patient when the injection device is in use. The "forward" end of the injection device is the end nearest the patient's skin when the device is in use. Similarly, reference to a "rearward" direction means the direction which is away from the patient and the "rearward" end of the device is the end furthest from the patient's skin when the injection device is in use.

Figure 1A:
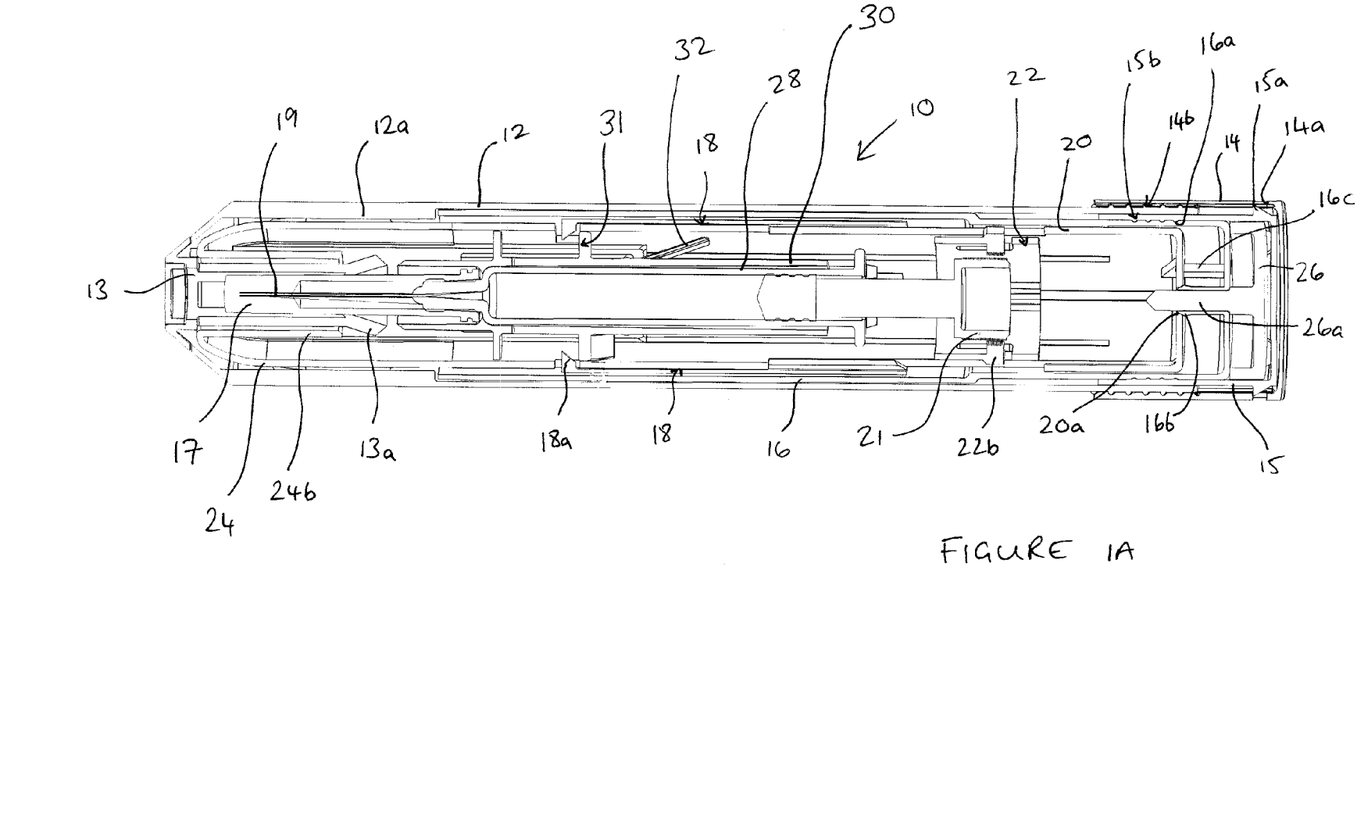
FIGS. 1A and 1B show mutually orthogonal cross-sectional views of an autoinjector device according to the present invention.
Figure 1B:
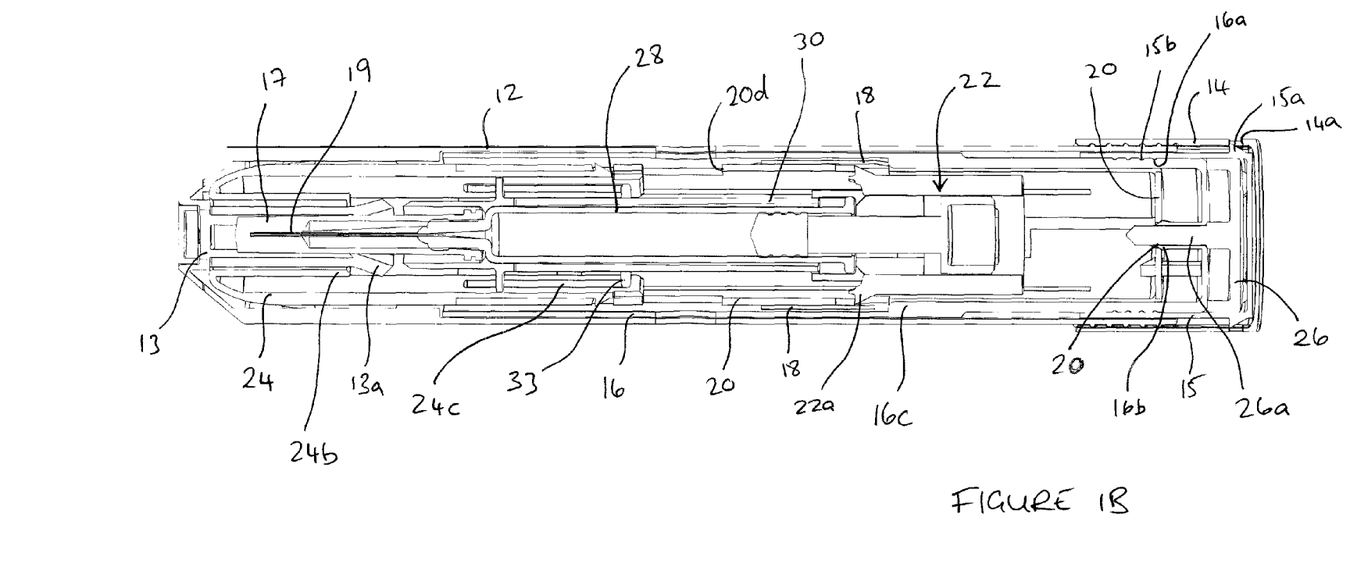

An exemplary embodiment 10 of an autoinjector according to the present invention is shown FIGS. 1A and 1B. The autoinjector 10 contains a syringe 28 having a needle 19 and may be actuated by a user to automatically deliver a dose of medicament to them self or another patient.

The autoinjector 10 is initially stored in an outer packaging 12 and a rear screw cap 14 screwed thereto via a screw thread 14b. The rear screw cap 14 surrounds a rear end cap 15 and has radial apertures 14a that radial projections 15a of the rear end cap 15 are located in. The rear end cap 15 is secured to an outer housing 16 of the autoinjector 10 via engagement between circumferential ribs 15b of the rear end cap 15 and complementary grooves 16a of the outer housing 16. When the ribs 15b are engaged with the grooves 16a, part of the rear end cap 15 is radially constrained between the outer housing 16 and the outer packaging 12, and the rear end cap 15 cannot disengage from the outer housing 16.

To remove the autoinjector 10 from the outer packaging 12, the user unscrews the rear screw cap 14 relative to the outer packaging 12. Because the rear end cap 15 is connected to the rear screw cap 14 and the rear end cap 15 is prevented from disengaging from the outer housing 16, the unscrewing of the rear screw cap 14 from the outer packaging 12 causes the outer packaging 12 to move axially forwardly relative to the rear screw cap 14 and the outer housing 16. Internal axial ribs 12a on the outer packaging 12 are guided in axial channels 24a (see FIGS. 2A and 2B) of a front housing 24 of the autoinjector 10 as the outer packaging 12 is unscrewed from the rear screw cap 14. The axial channels 24a prevent rotation of the axial ribs 12a (and therefore outer packaging 12) relative to the front housing 24 as the outer packaging 12 is unscrewed from the rear screw cap 14.

The forward end of the outer packaging 12 is attached to a needle sheath remover 13 which extends axially rearwardly from the front of the device. The needle sheath remover 13 has barbed legs 13a that are adapted to engage a needle sheath 17 into which the needle 19 of the device is staked in. As the outer packaging 12 moves axially forwardly relative to the outer housing 16 and front housing 24, the barbed legs 13a of the needle sheath remover 13 are drawn radially inwardly due to contact with an inward boss 24b of the front housing 24. As the barbed legs 13a are drawn radially inwardly, they bite into the needle sheath 17 and engage it such that further axial movement of the needle sheath remover 13 causes the needle sheath 17 to be axially withdrawn from the needle 19. Since the outer packaging 12 is prevented from rotating relative to the front housing 24 and outer housing 16 when being unscrewed from the rear screw cap 14, substantially no torque is transferred to the needle sheath remover 13, needle sheath 17 and, importantly, the needle 19, thereby minimising the risk of damage to the needle 19.

The syringe 28 does, however, experience a forward axial force as the needle sheath 17 is removed (since the sheath 17 is fitted over a front portion of the syringe 28). This tends to pull the internal components of the device (which are spring loaded) axially forwards and could result in damage if not controlled. In the present invention, this problem is mitigated by preventing the syringe 28 from moving axially forwards when the needle sheath 17 is removed. The syringe 28 is disposed in a syringe holder (syringe support means) 30 which supports the syringe 28 at a forward end and has a pair of tabs 31 projecting radially outwardly. The device further includes a rotating sleeve 18, intermediate the outer housing 16 and a rear housing 20 of the device, which is shown in more detail in FIGS. 2A, 2B and 3. The rotating sleeve 18 has a pair of radially inwardly projecting feet 18a which are each disposed at the end of an axially extending leg 18b of the rotating sleeve 18. As described below, the feet 18a act as blocking means which prevent the premature retraction of the needle 19. When assembled, the tabs 31 of the syringe holder 30 are axially aligned with the feet 18a of the rotating sleeve 18 so that forward axial movement of the syringe holder 30 relative to the rotating sleeve 18 is prevented which substantially prevents the syringe 18 moving axially forwards when the needle sheath 17 is removed. Consequently, the risk of damaging the internal components of the device when the needle sheath 17 is removed is significantly reduced.

Once the rearmost part of the outer packaging 12 moves axially past the front most part of the rear end cap 15, the ribs 15b can disengage from the grooves 16a (i.e. flex radially outwardly as they ride out of the grooves) and the rear screw cap 14 and rear end cap 15 can be removed from the device. Once the rear end cap 15 has been removed, the safety cap 26 can also be removed. The safety cap 26 has an axially forwardly projecting pin 26a that, when assembled, is located in an aperture 20a of a rear housing 20 of the device. In this position, the pin 26a also passes between radially flexible legs 16b of the outer housing 16, and prevents the legs from flexing radially inwardly thereby preventing them from passing through the aperture 20a of the rear housing. Due to this restriction, when the safety cap 26 is in place, the device cannot be actuated. Once the safety cap 26 is removed, the flexible legs 16b of the outer housing 16 can flex radially inwardly and are able to pass through the aperture 20a of the rear housing 20 thereby permitting axial movement of the outer housing 16 relative to the rear housing 20, which is necessary for actuation of the device. A hook 16c projecting axially forwardly from the rear of the outer housing 16 restricts rearward axial movement of the outer housing 16 relative to the rear housing 20 and prevents the two components from separating.

Figure 2A:
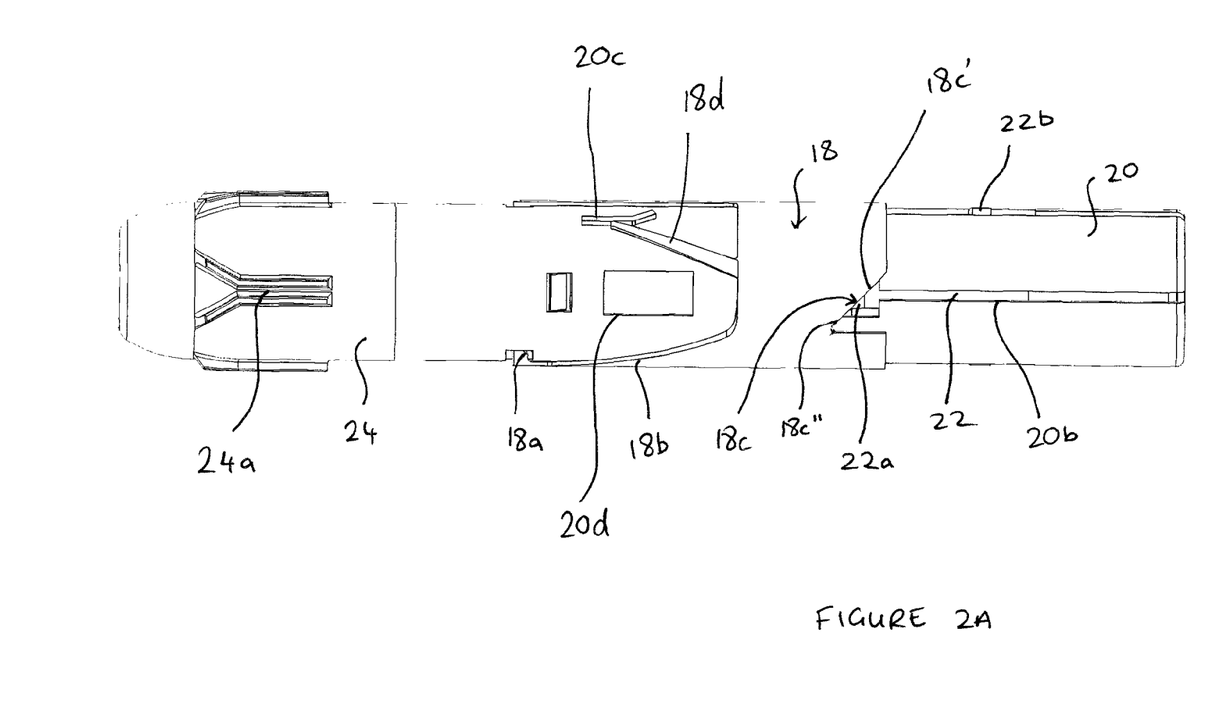
FIGS. 2A and 2B show side views of the autoinjector corresponding to FIGS. 1A and 1B respectively, where the outer packaging and outer housing have been removed for clarity.
Figure 2B:
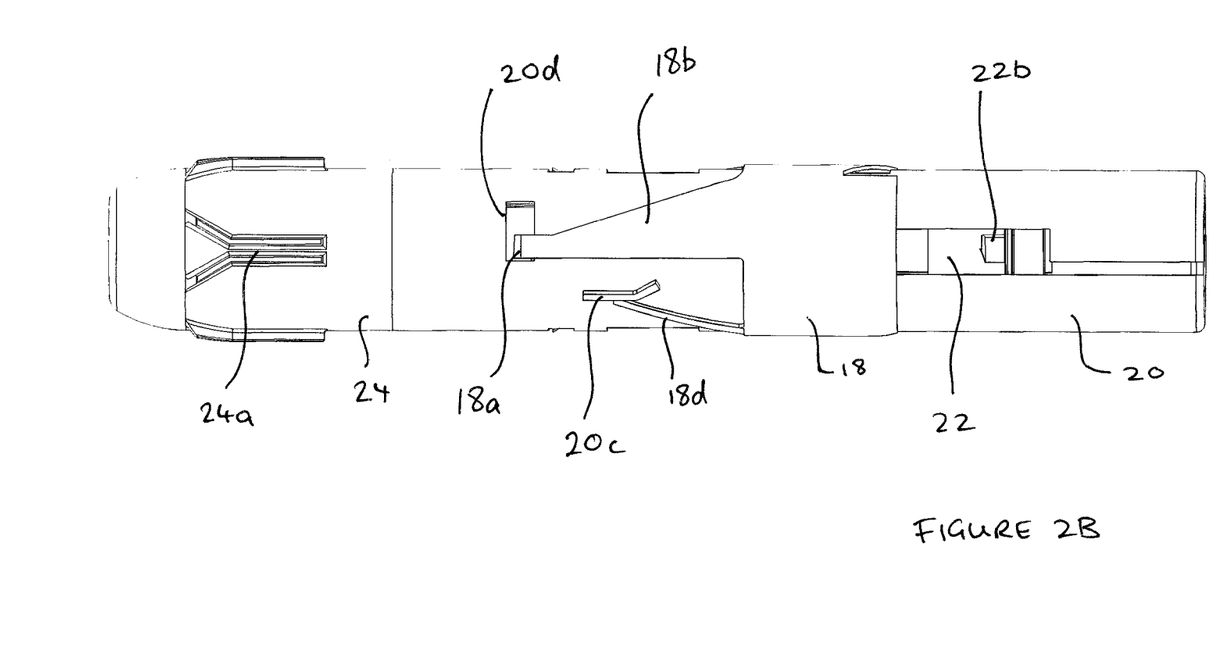
Figure 3:
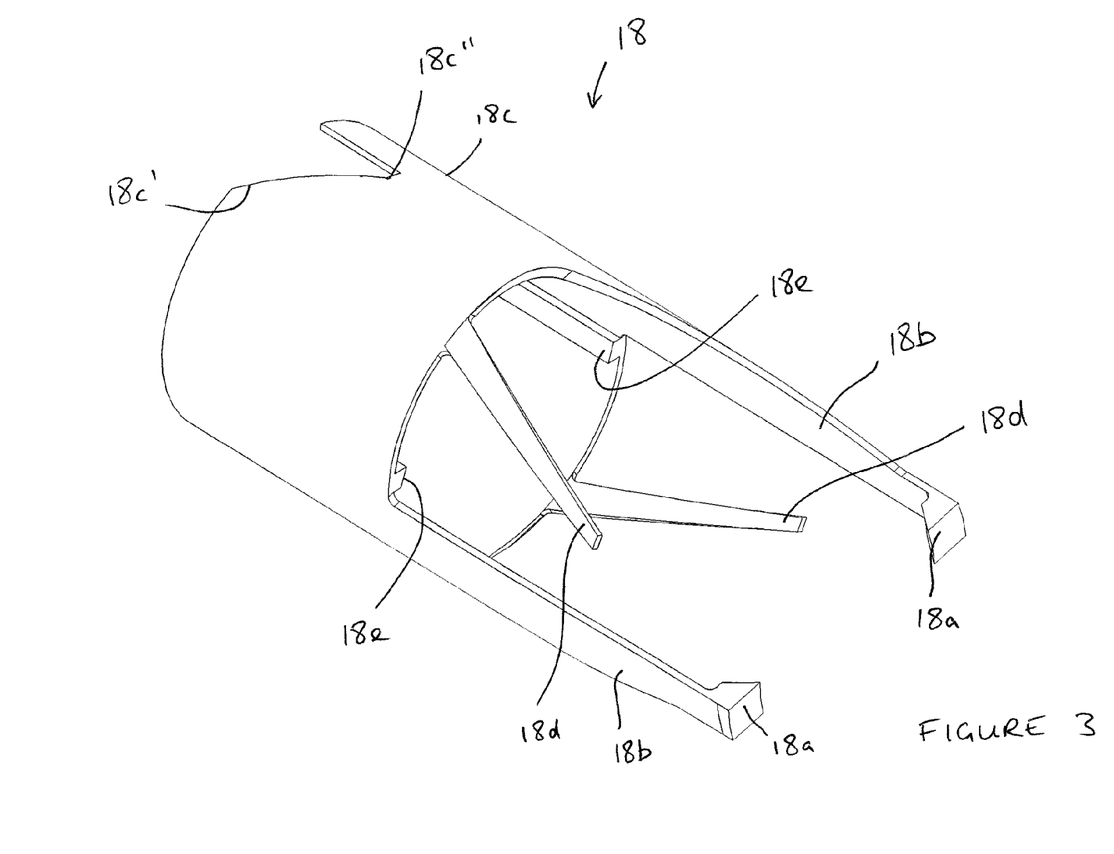
FIG. 3 shows a perspective view of the rotating sleeve.

Turning to FIGS. 2A and 2B, the rotating sleeve 18 is shown to have a sloped cut-out 18c in its rear end. The rotating sleeve 18 has a second identical sloped cut-out 18 diametrically opposite the one shown in the drawings. A pair of internal axially extending ribs 16c (see FIG. 1B) of the outer housing 16 are disposed in a pair of slots 20b of the rear housing and, prior to actuation of the device, are each in axial alignment with a shallow portion 18c' of one of the sloped cut-outs 18c. The rotating sleeve 18 also has a circumferentially flexible beam 18d extending in both an axial and a circumferential direction. Prior to actuation of the device, the beam 18d is in a relaxed state and the frontmost end of the beam 18d is in contact with a radial abutment 20c on the outer surface of the rear housing 20. The feet 18a of the rotating sleeve 18 are each disposed in a circumferential slot 20d in the rear housing 20.

To actuate the device, the user places the front end of the device against the injection site and pushes the outer housing 16 axially forwards towards the injection site. With the safety cap 26 removed, the outer housing 16 can move axially forwards relative to the rear housing 20 and as it does so, the ribs 16c of the outer housing 16 move axially along the slots 20b in the rear housing 20 and contact the shallow portion 18c' of the sloped cut-outs 18c. Continued axial forward movement of the outer housing 16 causes the ribs 16c to slide down the sloped cut-outs 18c towards deep portions 18c". However, given that the outer housing 16 is rotatably fixed with respect to the rear housing 20 due to engagement of the ribs 16c in the slots 20b, the contact between the ribs 16c and the sloped cut-outs causes the rotating sleeve 18 to rotate relative to the outer housing 16 and rear housing 18 from an initial ("second rotational") position to a fully rotated ("first rotational") position. In the fully rotated position, the beam 18d is flexed and stressed against abutment 20c which tends to bias the rotating sleeve 18 back to its initial position (although rotation back to the initial position is prevented by interference with the ribs 16c of the outer housing 16). When rotated, the feet 18a of the rotating sleeve 18 are out of axial alignment with the tabs 31 of the syringe holder 30 thereby permitting forward axial movement of the syringe holder 30 (and therefore, syringe 28) relative to the rear housing 20. Additionally, in this fully rotated position, internal axial ribs 18e of the rotating sleeve 18 are in axial alignment with radial abutment elements on rear legs (or tags) 22b of an inner housing 22 of the device, which is disposed within the rear housing 20. The forwardly moving ribs 16c also contact and move front legs (or tags) 22a of the inner housing 22 radially inwardly. In moving radially inwardly, the front legs 22a of the inner housing 22 move into axial alignment with the barrel of the syringe 28 and unlatch the inner housing 22 from the rear housing 20.

Unlatched, the inner housing 22 is free to move axially forwards under the influence of the drive spring (not shown). Given that the front legs 22a of the inner housing 22 are in axial alignment with the barrel of the syringe 28, continued forward movement of the inner housing 22 (under the influence of the drive spring—not shown) causes the syringe 28 and plunger rod 21 to move axially forwardly with no relative movement therebetween. This action drives the needle 19 out of the front of the device and into the injection site without expelling any medicament. As the inner housing 22 moves axially forwards, rear legs 22b of the inner housing 22 are drawn radially inwards (into contact with a plunger rod 21 of the syringe 28) by interference between the ribs 18e of the rotating sleeve 18 and the radially outwardly extending abutment elements on the rear legs 22b. At or around this time, the front legs 22a of the inner housing 22 become radially aligned with slots 20d in the rear housing 20 and flex radially outwardly (due to their inherent bias towards that position) out of engagement with the barrel of the syringe 28. Further forward axial movement of the inner housing 22 causes the rear legs 22b of the inner housing 22 to move the plunger rod 21 axially forwardly relative to the barrel of the syringe 28 and expel medicament from the needle 19 into the injection site.

Figure 4:
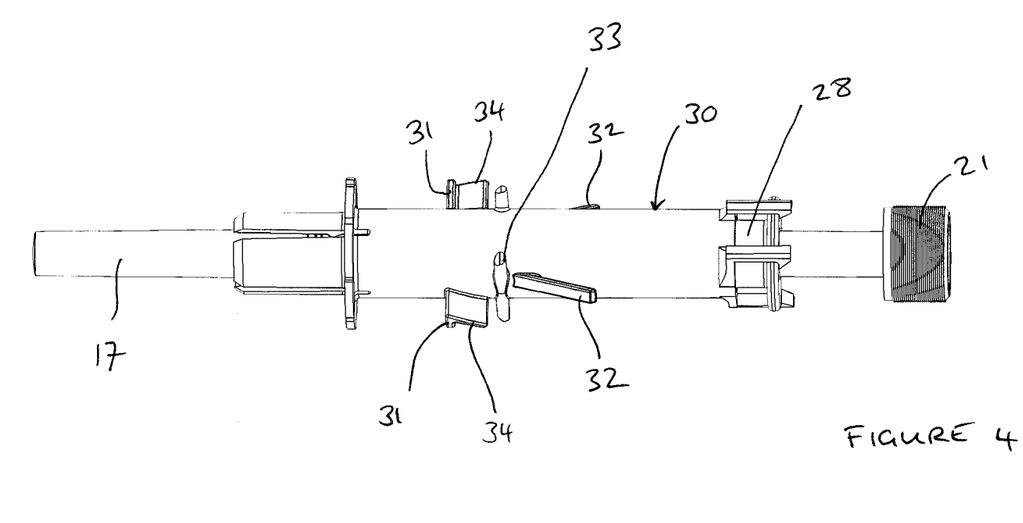
FIGS. 4 and 5 show side views of the autoinjector of FIGS. 1 and 2, where certain components have been removed to show the syringe holder.
Figure 5:
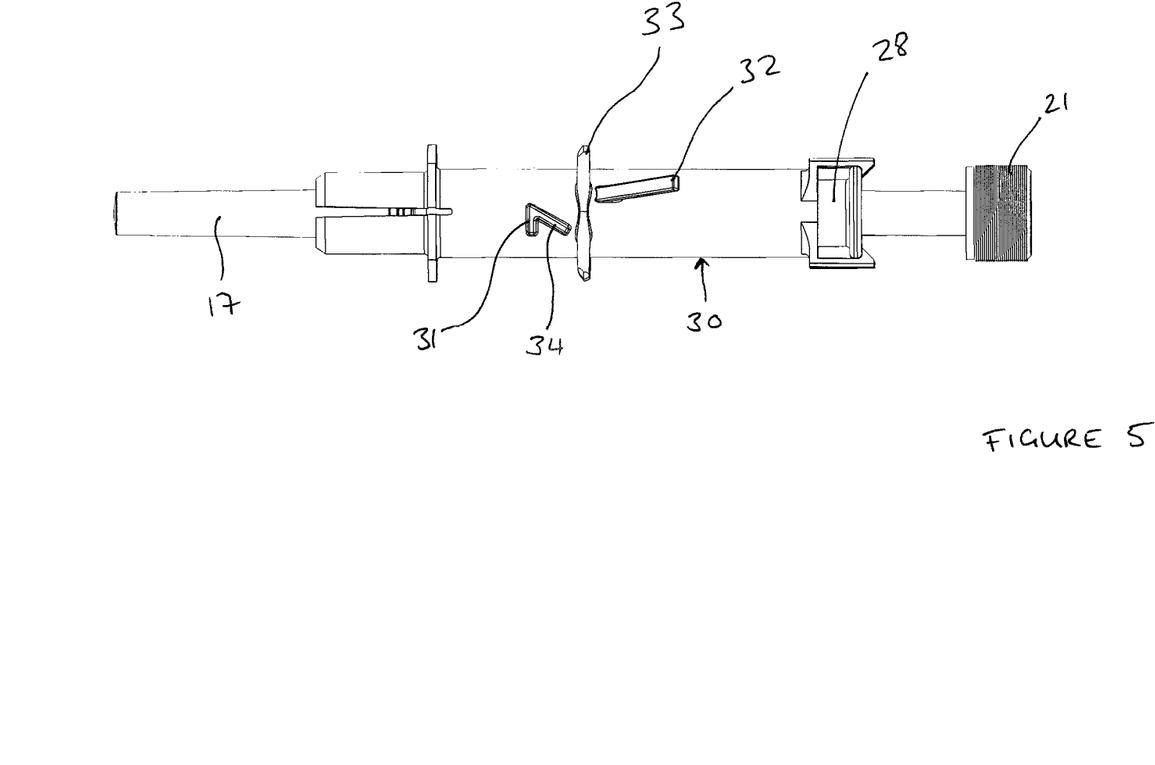

As shown in FIGS. 4 and 5, the syringe holder 30 includes a pair of flexible wings (or beams) 32 that are axially rearward of tabs 31 and circumferentially offset therefrom. Each flexible wing 32 extends both axially rearwardly and radially outwardly, when in a relaxed state. When the rotating sleeve 18 is rotated to its fully rotated position, the feet 18a of the rotating sleeve are each in axial alignment with one of the flexible wings 32 of the syringe holder 30. Guide arms 33 on the syringe holder 30 locate in slots 24c (see FIG. 1B) of the front housing 24 to only permit axial relative displacement between the syringe holder 30 and front housing 24. Additionally, FIGS. 4 and 5 show the tabs 31 in greater detail which each extend circumferentially on the surface of the syringe holder 30. Each tab 31 also has a "guide rib" sloped section 34, which extends both circumferentially and axially rearwardly on the surface of the syringe holder 30. The shape of the tabs 31 and guide ribs 34 permits efficient assembly of the device, whereby the feet 18a of the rotating sleeve 18 are able to ride down the guide ribs 34 during installation onto the rear housing 20. Given that the beam 18d becomes stressed against the abutment 20c on the rear housing 20 as the feet 18a ride along the guide ribs 34, the rotating sleeve 18 immediately rotates back to a relaxed position once the feet 18a are axially forwards of the tabs 31 so that the feet 18a are in axial alignment with the tabs 31.

As the inner housing 22 moves the syringe holder 30 axially forwards, the flexible wings 32 contact the feet 18a of the syringe holder 30 and flex radially inwardly. Further forward movement of the syringe holder 30 relative to the rotating sleeve 18 causes the flexible wings 32 to move axially forwards of the feet 18a and out of radial alignment with them, so that the wings 32 can flex radially outwardly once more. In this position, the syringe holder 30 is prevented from moving axially rearwardly relative to the rotating sleeve 18 (and therefore the rear housing 20) by axial abutment between the flexible wings 32 and the feet 18a of the rotating sleeve. It is this abutment that prevents automatic retraction of the syringe 28 occurring (under the influence of a retraction spring—not shown).

The inner housing 22 will continue to move the plunger rod 21 axially forwardly relative to the syringe 28 (expelling medicament from the needle 19 all the while), until the front legs 22a, which are moving along slots 20d of the rear housing 20, reach the forward ends of the slots 20d. This arrests movement of the inner housing 22 and therefore arrests further forward movement of the plunger rod 21 relative to the syringe 28 caused by the force of the drive spring. However, although the device has ceased to deliver the medicament, the needle 19 is still protruding from the front of the device, and the return spring (not shown) will begin to act rearwardly on the syringe 28. Since the inner housing 22, biased forwardly by the drive spring, is stationary, any rearward movement of the syringe 28 would cause some further medicament to exit the needle 19, which is not desirable. In the embodiment of the invention shown in the drawings, the axial engagement between the wings 32 of the syringe holder 30 and the feet 18a of the rotating sleeve 18 prevent rearward movement of the syringe 28 and prevent any further medicament from being expelled through the needle 19. This embodiment has the advantage that the device can deliver a partial dose of medicament, i.e. not discharge the entire contents of the syringe 28 (such as a discharge 0.3 ml from a total volume of 1 ml). The length of the slots 20d in the rear housing 20 can determine the volume of the delivered dose by determining the axial position that forward axial movement of the inner housing is arrested at. The axial engagement (axial "blocking") of the wings 32 and feet 18a and the radial engagement (radial "gripping") of the rear legs 22b of the inner housing 22 on the plunger rod 21 both serve to prevent retraction of the needle after the dose (full or partial) has been delivered.

In alternative embodiments, it may be desirable to allow the stopper on the front end of the plunger rod 21 to reach the forward end of the barrel of the syringe 28 and deliver the entire dose of medicament (unlike the embodiment described above with reference to the drawings). In these embodiments, the forward axial movement of the inner housing 22 will be arrested when the stopper "bottoms out" at the front end of the barrel of the syringe 28. Therefore, once movement of the inner housing 22 has arrested, the forward axial force from the drive spring continues to act on the syringe 28 and syringe holder 30 through the inner housing 22 and plunger rod 21. Consequently, the return spring is unable to move the syringe holder 30 and syringe 28 rearwards (since the forward force from the drive spring is greater in magnitude than the rearward force from the retraction spring). Regardless of rearward movement of the syringe 28, there is no risk of continued expulsion of medicament from the needle 19 since the entire dose has already been delivered. It follows that in these embodiments, the wings 32 and feet 18a are not necessarily essential to the operation of the invention, although they may still be employed to provide additional engagement means for preventing retraction of the needle 19. Absent the wings 32 and feet 18a, the engagement means are provided solely by the engagement of the rear legs 22b of the inner housing 22 on the plunger rod 21. The rear legs 22b may engage the plunger rod 21 by radially gripping it, as shown in the drawings, or by axially blocking it, by moving radially to a point in axial alignment and axially rear of the plunger rod 21.

When retraction is desired, the user removes the forward pressure on the outer housing 16 thus allowing the outer housing 16 to move rearwardly relative to the rear housing 20 to its initial position, under the influence of a spring or other biasing means (not shown). As the outer housing 16 moves axially rearwards relative to the rear housing 20, the ribs 16c of the outer housing 16 no longer force the rotating sleeve 18 to its fully rotated position, thus allowing the rotating sleeve 18 to rotate back towards its initial position under the biasing influence of the stressed beam 18d. Once the rotating sleeve 18 has rotated back to its initial position, the feet 18a of the rotating sleeve 18 are no longer axially aligned with the flexible wings 32 of the syringe holder 30. Additionally, the ribs 16c of the outer housing 16 move out of axial alignment with the rear legs 22b of the inner housing 22. Thus, when the rotating sleeve moves back to its initial position, the syringe holder 30 is able to move axially rearwards relative to the rear housing 20 (retracting the needle 29 from the injection site as it does so), and the rear legs 22b of the inner housing are able to relax, moving radially outward, out of engagement with the plunger rod 21.

Therefore the action of releasing the forward pressure on the outer housing 16 allows retraction of the needle 19 and halts delivery of medicament, if delivery of the intended dose has not been completed. Consequently, the present invention provides a reliable and efficient means for controlling the retraction of a needle after or during delivery of medicament without the risk of medicament exiting the needle during retraction.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An autoinjector including
   a housing, in which can be mounted a syringe having a plunger, a barrel and a needle at one end thereof through which medicament can be delivered to an injection site;
   a syringe support capable of causing said syringe to move along an axial path with respect to said housing; and
   a biasing member capable of biasing said syringe support so that said needle is normally inside said housing;
   wherein said housing includes an outer housing and said autoinjector further comprises a sleeve concentrically intermediate of said syringe support and said outer housing, wherein said sleeve is capable of rotating about a longitudinal axis of said autoinjector between a first rotational position and a second rotational position;
   said sleeve including an engagement mechanism that is selectively moveable by a user from a first position to a second position by rotation of said sleeve from said first rotational position to said second rotational position;
   wherein in said first position said engagement mechanism engages with said syringe support to substantially prevent rearward movement of said syringe along said axial path when said syringe is in an extended position where at least part of said needle is out of said housing, and in said second position rearward movement of said syringe along said axial path relative to said housing is possible and said biasing member causes said needle to retract inside said housing; and wherein said sleeve is moveable between said first and second rotational positions by moving said outer housing rearwardly with respect to said sleeve and said engagement mechanism in a substantially axial direction.

2. An autoinjector according to claim 1, wherein said housing further includes an inner housing, at least part of which is positionable, in use, intermediate said outer housing and said syringe support; and a rear housing intermediate said outer housing and said inner housing, and wherein said autoinjector further comprises an energy source in communication with said inner housing, said inner housing being moveable by said energy source between three positions, namely a first position in which said inner housing is in communication with said barrel such that, in use, said plunger and barrel are movable axially so as to move at least part of said needle out of said outer housing;

a second position in which said inner housing is in communication with said plunger but not said barrel such that, in use, said plunger is movable axially into said barrel so as to expel medicament through said needle; and a third position in which said inner housing is in communication with neither said plunger nor said barrel such that, in use, said plunger and barrel are able to retract in order to retract said needle into said outer housing.

3. An autoinjector according to claim 2, wherein said inner housing comprises a set of rear tags and a set of forward tags where said rear tags are capable of communicating with said plunger and said forward tags are capable of communicating with said barrel.

4. An autoinjector according to claim 3, wherein said rear tags and said forward tags are radially flexible.

5. An autoinjector according to claim 3, wherein said rear housing comprises apertures and said front tags are capable of flexing radially outwardly into said apertures into said second position where said inner housing is not in communication with said barrel.

6. An autoinjector according to claim 4, wherein said longitudinal ribs are tapered at a rear end in an axial direction.

7. An autoinjector according to claim 4, wherein said sleeve comprises a plurality of longitudinal ribs on an inner surface of said sleeve, and an outer surface of each rear tag of said inner housing has a radially extending abutment element where said abutment elements are axially aligned with said longitudinal ribs when said sleeve is in said first rotational position.

8. An autoinjector according to claim 7, wherein each of said abutment elements are tapered in a circumferential direction.

9. An autoinjector according to claim 7, wherein said engagement mechanism includes said rear tags, wherein abutment between said longitudinal ribs and said abutment elements causes said rear tags to flex radially inwardly into communication with said plunger when said sleeve is in said first rotational position.

10. An autoinjector according to claim 9, wherein said communication between said rear tags and said plunger is radial gripping of said rear tags on said plunger.

11. An autoinjector according to claim 9, wherein said communication between said rear tags and said plunger is axial blocking of said plunger by said rear tags, where said rear tags are axially aligned with and axially rearward of said plunger.

12. An autoinjector according to claim 1, wherein said engagement mechanism is selectively moveable by a user from said first position to said second position by the release or reduction of a previously-applied forward force.

13. An autoinjector according to claim 12, wherein said engagement mechanism is selectively moveable by a user from said first position to said second position by the release or reduction of said previously-applied forward force after delivery of a partial, but not necessarily complete, dose of medicament.

14. An autoinjector according to claim 1, wherein said sleeve comprises a sleeve-biasing member for urging said sleeve towards said second rotational position.

15. An autoinjector according to claim 1, wherein said housing further comprises a front housing, said front housing being disposed at least partially within said outer housing at a forward end of said autoinjector; and wherein engagement between said syringe support and said front housing restricts movement of said syringe support to axial movement relative to said front housing.

16. An autoinjector according to claim 15, wherein said front housing has a plurality of axial slots and said syringe support includes projections that engage with said axial slots to restrict said relative movement between said syringe support and said front housing to relative axial movement.

17. An autoinjector according to claim 1, wherein said sleeve comprises a plurality of legs projecting axially forwardly, wherein said legs each have a foot projecting radially inwardly.

18. An autoinjector according to claim 17, wherein said syringe support comprises a plurality of tabs projecting radially outwardly and said tabs are axially aligned with said feet when said sleeve is in said second rotational position.

19. An autoinjector according to claim 18, wherein forward axial movement of said syringe support relative to said sleeve is substantially prevented by abutment between said tabs and said feet when said sleeve is in said second rotational position and said tabs are disposed axially rearwards of said feet.

20. An autoinjector according to claim 18, wherein said tabs comprise guide ribs that extend in both an axially rearward direction and a circumferential direction from said tabs, where, during assembly of said autoinjector, said guide ribs are capable of abutting said feet and rotating said sleeve away from said second rotational position so that said feet can move from a position axially rearward of said tabs to a position axially forward of said tabs.

21. An autoinjector according to claim 20, wherein said sleeve is capable of rotating back to said second rotational position when said feet are positioned axially forward of said tabs, and said sleeve further comprising a sleeve-biasing member for urging said sleeve towards said second rotational position.

22. An autoinjector according to claim 17, wherein said feet are generally wedge-shaped.

23. An autoinjector according to claim 17, wherein said engagement mechanism forms part of said sleeve, said engagement mechanism engages with said syringe support to substantially prevent rearward movement of said syringe along said axial path when in said first position, and said engagement mechanism includes a blocking mechanism which comprises said feet and a plurality of flexible beams are each connected to said syringe support at a proximal end and extend both radially outwardly and axially rearwardly to a distal end, wherein each of said beams are axially aligned with one of said feet, respectively, when said sleeve is in said first rotational position, such that in use, as said syringe support moves axially forward relative to said sleeve, said beams are capable of contacting said respective feet and deflecting radially inwardly until said distal ends are axially forwards of said feet and when positioned axially forwards of said feet said beams are capable of flexing radially outwards to a position where said distal ends are axially aligned with or radially beyond said feet.

* * * * *